United States Patent [19]

Salmond et al.

[11] Patent Number: 5,821,077
[45] Date of Patent: Oct. 13, 1998

[54] PROCESS FOR ACTIVATING GENE EXPRESSION IN BACTERIA

[75] Inventors: George Peacock Copland Salmond, Leamington Spa; Matthew Thomas Geoffrey Holden, Coventry; Anthony Richard John Cox, Solihull; Nicholas Robert Thomson; Simon James McGowan, both of Conventry, all of Great Britain

[73] Assignee: University of Warwick, Coventry, United Kingdom

[21] Appl. No.: 553,633

[22] PCT Filed: May 25, 1994

[86] PCT No.: PCT/GB94/01141

§ 371 Date: Apr. 1, 1996

§ 102(e) Date: Apr. 1, 1996

[87] PCT Pub. No.: WO94/28135

PCT Pub. Date: Dec. 8, 1994

[30] Foreign Application Priority Data

Jun. 1, 1993 [GB] United Kingdom .................. 9311641

[51] Int. Cl.⁶ ........................................................ C12P 1/00
[52] U.S. Cl. .......................... 435/41; 435/69.1; 435/713; 530/350; 536/23.1
[58] Field of Search .......................... 435/69.1, 6, 172.1, 435/320.1, 41, 71.1, 71.2, 71.3; 935/29, 36, 38, 72, 79; 536/23.1

[56] References Cited

PUBLICATIONS

Lewin, B., ed., 1983, Genes, John Wiley and Sons, see especially Chapter 15, pp. 247–249, 1983.

*Primary Examiner*—Nancy Degen
*Assistant Examiner*—Irem Yucel
*Attorney, Agent, or Firm*—Birch, Stewart, Kolasch & Birch, LLP

[57] ABSTRACT

A DNA sequence encoding the CarR gene product or a homologue or variant thereof which, on expression in bacteria, is capable of activating gene expression, especially of a gene coding for a carbapenem antibiotic. A polypeptide coded for by such DNA.

18 Claims, 6 Drawing Sheets

FIG. 1A

```
GAAGATGCGAATTTCGAAAAATGTATGAAGAATCATGAAAAATGATTTGCAGAGATGTTACTT
 E  D  A  N  F  E  K  C  M  K  N  H  E  N  D  L  Q  M  L  L
GTGAATGTACATGAAAAAGTGATGGCCTATCAGCGAGCTATCAACGATCAAGATAACCCC
 V  N  V  H  E  K  V  M  A  Y  Q  R  A  I  N  D  Q  D  N  P
CCCGATAATTCAAGAAACGCCCTTACTCTCTCCGCGTGAAACCGAAGTTCTTTTCCTGGTT
 P  D  N  S  R  N  A  L  L  S  P  R  E  T  E  V  L  F  L  V
AGTAGTGGACGAACTTACAAAGAGGTTTCCCGTATATTAGGTATTGATGGAGGTCACCGTT
 S  S  G  R  T  Y  K  E  V  S  R  I  L  G  I  S  E  V  T  V
AAGTTCCACATTAACAACTCAGTCCGTAAATTGGATGTGTTATCAATTCCCGCCATGCTATA
 K  F  H  I  N  N  S  V  R  K  L  D  V  I  N  S  R  H  A  I
ACTAAAGCACTTGAGTTAAATCTTTTCCATTCCCCCTGTGAACCTGTAGTGATGAAGCAT
 T  K  A  L  E  L  N  L  F  H  S  P  C  E  P  V  V  M  K  H
ATGGACGCCCGTTAG
 M  D  A  R  *
```

FIG.1B

```
                                                                    SspI
                                                           TTATAATAATAGTAACT
CTATCAATTATTATTGAATTATTAGTATATAAAATGTTGACTGATTGTATATTAATTGAT
AACTTTCGACCTTGTTAAATCCTAGTGATTATATTGGTGTAACTAAAAATAATTATATT
TACTCTCTGGTAAAGAGTTGATCTTTTAATCTTTGAGCAAAGTCGGTAAGAGAGGGTAAT
ATGGATCATGAAATCCATTCCTTTATCAAAGGAAGTTGAAAGGAGTCGGTGATGTATGG
 M  D  H  E  I  H  S  F  I  K  R  K  L  K  G  V  G  D  V  W
TTTTCTTATTTTATGATGAGTAAAAACTCTACCAGCCAACCTTATATTATTTCGAATTAT
 F  S  Y  F  M  M  S  K  N  S  T  S  Q  P  Y  I  I  S  N  Y
CCAGAAGCATGGATGAAGGAGTATATAAAAAAGAGATGTTTCTGAGTGATCCTATCATT
 P  E  A  W  M  K  E  Y  I  K  K  E  M  F  L  S  D  P  I  I
GTTGCCTCATTAGCTCGGATCACGCCGTTTCTTGGGATGATAATGATATTGTGACGCTA
 V  A  S  L  A  R  I  T  P  F  S  W  D  D  N  D  I  V  T  L
AGAGCCAAGAATCAGGATGTCTTTATTTCTTCCGTGCAGCACGATATAAGTTCAGGTTAT
 R  A  K  N  Q  D  V  F  I  S  S  V  Q  H  D  I  S  S  G  Y
ACCTTTGTTTTGCACGACCATGATAATAATGTGGGCGACACTGAGTATAGCGAATCACTTG
 T  F  V  L  H  D  H  D  N  N  V  A  T  L  S  I  A  N  H  L
```

FIG.2A

```
GAAGATGCGAATTTCGAAAAATGTATGAAGAATCATGAAAAATGATTTGCAGATGTTACTT
 E  D  A  N  F  E  K  C  M  K  N  H  E  N  D  L  Q  M  L  L

GTGAATGTACATGAAAAAGTGATGGCCTATCAGCGAGCTATCAACGATCAAGATAACCCC
 V  N  V  H  E  K  V  M  A  Y  Q  R  A  I  N  D  Q  D  N  P

CCCGATAATTCAAGAAACGCCTTACTCTCTCCGCGTGAAACCGAAGTTCTTTTCCTGGTT
 P  D  N  S  R  N  A  L  L  S  P  R  E  T  E  V  L  F  L  V

AGTAGTGGACGAACTTACAAAGAGGTTTCCCGTATATTAGGTATTAGTGAGGTCACCGTT
 S  S  G  R  T  Y  K  E  V  S  R  I  L  G  I  S  E  V  T  V

AAGTTCCACATTAACAACTCACTCCGTAAATTGGATGTTATCAATTCCCGCCATGCTATA
 K  F  H  I  N  N  S  V  R  K  L  D  V  I  N  S  R  H  A  I

ACTAAAGCACTTGAGTTAAATCTTTTCCATTCCCCCTGTGAACCTGTAGTGATGAAGCAT
 T  K  A  L  E  L  N  L  F  H  S  P  C  E  P  V  V  M  K  H

ATGGACGCCCGTTAGCGTGTATTAATGCTTGATAATAGGGAGGTACCTATCCAAAAGAAT
 M  D  A  R  *

AGTAACTCCCTATCTAAAAGAAATACATTAGCTGAACTTTTACACGGTTAATATT
                                                    SspI
```

FIG.2B

```
                                                      HinfI
                                                       GAT
TCGAATTATTTAAGGTGTGTGTTTAGTTAATATGAATATAAAATGTTGACGAATTGTTTATG

CATTGATATGGTTGGTAACCATTAGAGTCATGATGTTACATATCAATAATGACTGGG

CTTGTTTTATCAGGGAAAATATCGGTAATTCTCGCGTTTTTACTAATATTTCTGGGAA

TATTGTTGATGAATAAAGAGATCAGTTATTTTATAGAAAGAAAGCTAAAGGCCTATGGGA
              M  N  K  E  I  S  Y  F  I  E  R  K  L  K  A  Y  G

ATGTTTTATTCGCTTACTTTATGATGGATAAATCTTCTTTATCAAATCCTGTTTTTATTT
 N  V  L  F  A  Y  F  M  M  D  K  S  S  L  S  N  P  V  F  I

CTAACTACCCCCAAAAATGTATTGATACCTATATTGATAATAAACTTTTTATCAATGATC
 S  N  Y  P  Q  K  C  I  D  T  Y  I  D  N  K  L  F  I  N  D

CTGTTATACATTACTCTTTAAAAAGAGTAACTCCATTTTCCTGGGATGATAACGATCTCG
 P  V  I  H  Y  S  L  K  R  V  T  P  F  S  W  D  D  N  D  L

CTGTATTACGGTCCGAAAATGAAGATGTTGCCATGTATCTAAGGGAGCATGACATCACTG
 A  V  L  R  S  E  N  E  D  V  A  M  Y  L  R  E  H  D  I  T

TAGGTTACACATTTGTTCTTCACGACCATGATAACAATCTGGCGATCCTGACTATTGCTA
 V  G  Y  T  F  V  L  H  D  H  D  N  N  L  A  I  L  T  I  A

FIG.3A
```

```
ACAATGATGAAAAAAATGATTTTGAGGATTTTATAAAGAACAGAGAGAATGATTTACAAA
 N  N  D  E  K  N  D  F  E  D  F  I  K  N  R  E  N  D  L  Q

TGTTGTTAGTGACTACTCACGAAAAAGCAATGAAACATAAACACTTCGTTAAAGGTAAAA
 M  L  V  T  T  H  E  K  A  M  K  H  K  H  F  V  K  G  K

CGGGCGCCCTTGGATTGCTTGCAAAGTGCATTGATTACACCACGTGAAACAGAAGTACTTT
 T  A  P  L  D  C  L  Q  S  A  L  I  T  P  R  E  T  E  V  L

TCTTGGTCAGTAGAGGGAATACTTATAAAGAGGTGTCCAGAACACTGGGTATCAGTGAAG
 F  L  V  S  R  G  N  T  Y  K  E  V  S  R  T  L  G  I  S  E

CAACAGTGAAATTCCATATCAATAACTCTGTCAGAAAACTTAATGTCATTAATTCTCGCC
 A  T  V  K  F  H  I  N  N  S  V  R  K  L  N  V  I  N  S  R

ATGCCATAAGCAAAGCACTTGAGCTCAATCTGTTTCGAGCCTTTACGGGATCTCTCATGA
 H  A  I  S  K  A  L  E  L  N  L  F  R  A  F  T  G  S  L  M

CCAGAAAATTGGTTGCAATATAGTATATTTAATACTTATATTTCGTTATATGGCTGACC
 T  R  K  L  V  A  I  *

AACCTTTAGATGATGATGCTGTACATCTCTATTACCTATATAAAAGAATATCACCTATACCA

ATAATATTTTCAGACTATTCTTTTACGAAGGTTGTTTTTTATCTGATTAGTTATAATTA

ACGCAGAATTAAAAATCGAT
```

FIG. 3B

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
        ( A ) LENGTH: 735 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Erwinia carotovora ( x i ) SEQUENCE DESCRIPTION: SEQ ID NO: 1:

| | | | | | |
|---|---|---|---|---|---|
| ATGGATCATG | AAATCCATTC | CTTTATCAAA | AGGAAGTTGA | AAGGAGTCGG | TGATGTATGG | 60
| TTTTCTTATT | TTATGATGAG | TAAAAACTCT | ACCAGCCAAC | CTTATATTAT | TTCGAATTAT | 120
| CCAGAAGCAT | GGATGAAGGA | GTATATAAAA | AAAGAGATGT | TTCTGAGTGA | TCCTATCATT | 180
| GTTGCCTCAT | TAGCTCGGAT | CACGCCGTTT | TCTTGGGATG | ATAATGATAT | TGTGACGCTA | 240
| AGAGCCAAGA | ATCAGGATGT | CTTTATTTCT | TCCGTGCAGC | ACGATATAAG | TTCAGGTTAT | 300
| ACCTTTGTTT | TGCACGACCA | TGATAATAAT | GTGGCGACAC | TGAGTATAGC | GAATCACTTG | 360
| GAAGATGCGA | ATTTCGAAAA | ATGTATGAAG | AATCATGAAA | ATGATTTGCA | GATGTTACTT | 420
| GTGAATGTAC | ATGAAAAAGT | GATGGCCTAT | CAGCGAGCTA | TCAACGATCA | AGATAACCCC | 480
| CCCGATAATT | CAAGAAACGC | CTTACTCTCT | CCGCGTGAAA | CCGAAGTTCT | TTTCCTGGTT | 540
| AGTAGTGGAC | GAACTTACAA | AGAGGTTTCC | CGTATATTAG | GTATTAGTGA | GGTCACCGTT | 600
| AAGTTCCACA | TTAACAACTC | AGTCCGTAAA | TTGGATGTTA | TCAATTCCCG | CCATGCTATA | 660
| ACTAAAGCAC | TTGAGTTAAA | TCTTTTCCAT | TCCCCCTGTG | AACCTGTAGT | GATGAAGCAT | 720
| ATGGACGCCC | GTTAG | | | | | 735

( 2 ) INFORMATION FOR SEQ ID NO: 2:

( i ) SEQUENCE CHARACTERISTICS:
( A ) LENGTH: 244 amino acids
( B ) TYPE: amino acid
( D ) TOPOLOGY: linear ( i i ) MOLECULE TYPE: protein ( v i ) ORIGINAL SOURCE:
( A ) ORGANISM: Erwinia carotovora ( x i ) SEQUENCE DESCRIPTION: SEQ ID NO: 2:

| Met | Asp | His | Glu | Ile | His | Ser | Phe | Ile | Lys | Arg | Lys | Leu | Lys | Gly | Val |
|---|---|---|---|---|---|---|---|---|---|---|---|---|---|---|---|
| 1 | | | | 5 | | | | | 10 | | | | | 15 | |

| Gly | Asp | Val | Trp | Phe | Ser | Tyr | Phe | Met | Met | Ser | Lys | Asn | Ser | Thr | Ser |
| | | | 20 | | | | | 25 | | | | | 30 | | |

| Gln | Pro | Tyr | Ile | Ile | Ser | Asn | Tyr | Pro | Glu | Ala | Trp | Met | Lys | Glu | Tyr |
| | | 35 | | | | | 40 | | | | | 45 | | | |

| Ile | Lys | Lys | Glu | Met | Phe | Leu | Ser | Asp | Pro | Ile | Ile | Val | Ala | Ser | Leu |
| | 50 | | | | | 55 | | | | | 60 | | | | |

| Ala | Arg | Ile | Thr | Pro | Phe | Ser | Trp | Asp | Asp | Asn | Asp | Ile | Val | Thr | Leu |
| 65 | | | | | 70 | | | | | 75 | | | | | 80 |

| Arg | Ala | Lys | Asn | Gln | Asp | Val | Phe | Ile | Ser | Val | Gln | His | Asp | Ile |
| | | | | 85 | | | | | 90 | | | | | 95 | |

| Ser | Ser | Gly | Tyr | Thr | Phe | Val | Leu | His | Asp | His | Asp | Asn | Asn | Val | Ala |
| | | | 100 | | | | | 105 | | | | | 110 | | |

| Thr | Leu | Ser | Ile | Ala | Asn | His | Leu | Glu | Asp | Ala | Asn | Phe | Glu | Lys | Cys |
| | | 115 | | | | | 120 | | | | | 125 | | | |

| Met | Lys | Asn | His | Glu | Asn | Asp | Leu | Gln | Met | Leu | Leu | Val | Asn | Val | His |
| | 130 | | | | | 135 | | | | | 140 | | | | |

| Glu | Lys | Val | Met | Ala | Tyr | Gln | Arg | Ala | Ile | Asn | Asp | Gln | Asp | Asn | Pro |
| 145 | | | | | 150 | | | | | 155 | | | | | 160 |

| Pro | Asp | Asn | Ser | Arg | Asn | Ala | Leu | Leu | Ser | Pro | Arg | Glu | Thr | Glu | Val |
| | | | | 165 | | | | | 170 | | | | | 175 | |

| Leu | Phe | Leu | Val | Ser | Ser | Gly | Arg | Thr | Tyr | Lys | Glu | Val | Ser | Arg | Ile |
| | | | 180 | | | | | 185 | | | | | 190 | | |

```
    Leu Gly Ile Ser Glu Val Thr Val Lys Phe His Ile Asn Asn Ser Val
        195                 200                 205

Arg Lys Leu Asp Val Ile Asn Ser Arg His Ala Ile Thr Lys Ala Leu
        210                 215                 220

Glu Leu Asn Leu Phe His Ser Pro Cys Glu Pro Val Val Met Lys His
    225                 230                 235                 240

Met Asp Ala Arg
```

( 2 ) INFORMATION FOR SEQ ID NO: 3:

( i ) SEQUENCE CHARACTERISTICS:
        ( A ) LENGTH: 1032 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Erwinia carotovora ( x i ) SEQUENCE DESCRIPTION: SEQ ID NO: 3:

```
TTATAATAAT  AGTAACTCTA  TCAATTATTA  TTGAATTATT  AGTATATAAA  ATGTTGACTG      60
ATTGTATATT  AATTGATAAC  TTTCGACCTT  GTTAAATCCT  AGTGATTATA  TTTGGTGTAA     120
CTAAAAATAA  TTATATTTAC  TCTCTGGTAA  AGAGTTGATC  TTTTAATCTT  TGAGCAAAGT     180
CGGTAAGAGA  GGGTAATATG  GATCATGAAA  TCCATTCCTT  TATCAAAAGG  AAGTTGAAAG     240
GAGTCGGTGA  TGTATGGTTT  TCTTATTTTA  TGATGAGTAA  AAACTCTACC  AGCCAACCTT     300
ATATTATTTC  GAATTATCCA  GAAGCATGGA  TGAAGGAGTA  TATAAAAAAA  GAGATGTTTC     360
TGAGTGATCC  TATCATTGTT  GCCTCATTAG  CTCGGATCAC  GCCGTTTTCT  TGGGATGATA     420
ATGATATTGT  GACGCTAAGA  GCCAAGAATC  AGGATGTCTT  TATTTCTTCC  GTGCAGCACG     480
ATATAAGTTC  AGGTTATACC  TTTGTTTTGC  ACGACCATGA  TAATAATGTG  GCGACACTGA     540
GTATAGCGAA  TCACTTGGAA  GATGCGAATT  TCGAAAAATG  TATGAAGAAT  CATGAAAATG     600
ATTTGCAGAT  GTTACTTGTG  AATGTACATG  AAAAAGTGAT  GGCCTATCAG  CGAGCTATCA     660
ACGATCAAGA  TAACCCCCCC  GATAATTCAA  GAAACGCCTT  ACTCTCTCCG  CGTGAAACCG     720
AAGTTCTTTT  CCTGGTTAGT  AGTGGACGAA  CTTACAAAGA  GGTTTCCCGT  ATATTAGGTA     780
TTAGTGAGGT  CACCGTTAAG  TTCCACATTA  ACAACTCAGT  CCGTAAATTG  GATGTTATCA     840
ATTCCCGCCA  TGCTATAACT  AAAGCACTTG  AGTTAAATCT  TTTCCATTCC  CCTGTGAAC      900
CTGTAGTGAT  GAAGCATATG  GACGCCCGTT  AGCGTGTATT  AATGCTTGAT  AATAGGGAGG     960
TACCTATCCA  AAAGAATAGT  AACTCCCTAT  CTAAAAGAAA  TACATTAGCT  GAACTTTTAC    1020
ACGGTTAATA  TT                                                            1032
```

( 2 ) INFORMATION FOR SEQ ID NO: 4:

( i ) SEQUENCE CHARACTERISTICS:
        ( A ) LENGTH: 1103 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Serratia ( x i ) SEQUENCE DESCRIPTION: SEQ ID NO: 4:

```
GATTCGAATT  ATTTAAGGTG  TGTTTAGTTA  ATATGAATAT  AAAATGTTGA  CGAATTGTTT      60
```

| ATGCATTGAT | ATGGTTGGTA | ACCATTAGAG | TCATGATGTT | ACATATCAAT | AATAATGACT | 120 |
| GGGCTTGTTT | TATCAGGGAA | AATATCGGTA | ATTCTCGCGT | TTTTTACTAA | TATTTTCTGG | 180 |
| GAATATTGTT | GATGAATAAA | GAGATCAGTT | ATTTTATAGA | AAGAAAGCTA | AAGGCCTATG | 240 |
| GGAATGTTTT | ATTCGCTTAC | TTTATGATGG | ATAAATCTTC | TTTATCAAAT | CCTGTTTTTA | 300 |
| TTTCTAACTA | CCCCCAAAAA | TGTATTGATA | CCTATATTGA | TAATAAACTT | TTTATCAATG | 360 |
| ATCCTGTTAT | ACATTACTCT | TTAAAAGAG | TAACTCCATT | TTCCTGGGAT | GATAACGATC | 420 |
| TCGCTGTATT | ACGGTCCGAA | AATGAAGATG | TTGCCATGTA | TCTAAGGGAG | CATGACATCA | 480 |
| CTGTAGGTTA | CACATTTGTT | CTTCACGACC | ATGATAACAA | TCTGGCGATC | CTGACTATTG | 540 |
| CTAACAATGA | TGAAAAAAT | GATTTGAGG | ATTTTATAAA | GAACAGAGAG | AATGATTTAC | 600 |
| AAATGTTGTT | AGTGACTACT | CACGAAAAG | CAATGAAACA | TAAACACTTC | GTTAAAGGTA | 660 |
| AAACGGCGCC | CTTGGATTGC | TTGCAAAGTG | CATTGATTAC | ACCACGTGAA | ACAGAAGTAC | 720 |
| TTTTCTTGGT | CAGTAGAGGG | AATACTTATA | AGAGGTGTC | CAGAACACTG | GGTATCAGTG | 780 |
| AAGCAACAGT | GAAATTCCAT | ATCAATAACT | CTGTCAGAAA | ACTTAATGTC | ATTAATTCTC | 840 |
| GCCATGCCAT | AAGCAAAGCA | CTTGAGCTCA | ATCTGTTTCG | AGCCTTTACG | GGATCTCTCA | 900 |
| TGACCAGAAA | ATTGGTTGCA | ATATAGTATA | TTTTAATACT | TATATTTCGT | TATATGGCTG | 960 |
| ACCAACCTTT | AGATGATGCT | GTACATCTAT | TACCTATATA | AAAGAATAGT | ATCACCTATA | 1020 |
| CCAATAATAT | TTTCAGACTA | TTCTTTTACG | AAGGTTGTTT | TTTTATCTGA | TTAGTTATAA | 1080 |
| TTAACGCAGA | ATTAAAAATC | GAT | | | | 1103 |

( 2 ) INFORMATION FOR SEQ ID NO: 5:

( i ) SEQUENCE CHARACTERISTICS:
        ( A ) LENGTH: 244 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Serratia ( x i ) SEQUENCE DESCRIPTION: SEQ ID NO: 5:

```
Met  Asn  Lys  Glu  Ile  Ser  Tyr  Phe  Ile  Glu  Arg  Lys  Leu  Lys  Ala  Tyr
 1              5                        10                       15

Gly  Asn  Val  Leu  Phe  Ala  Tyr  Phe  Met  Met  Asp  Lys  Ser  Ser  Leu  Ser
               20                       25                       30

Asn  Pro  Val  Phe  Ile  Ser  Asn  Tyr  Pro  Gln  Lys  Cys  Ile  Asp  Thr  Tyr
               35                       40                       45

Ile  Asp  Asn  Lys  Leu  Phe  Ile  Asn  Asp  Pro  Val  Ile  His  Tyr  Ser  Leu
         50                       55                       60

Lys  Arg  Val  Thr  Pro  Phe  Ser  Trp  Asp  Asp  Asn  Asp  Leu  Ala  Val  Leu
 65                       70                       75                       80

Arg  Ser  Glu  Asn  Glu  Asp  Val  Ala  Met  Tyr  Leu  Arg  Glu  His  Asp  Ile
                    85                       90                       95

Thr  Val  Gly  Tyr  Thr  Phe  Val  Leu  His  Asp  His  Asp  Asn  Asn  Leu  Ala
                   100                      105                      110

Ile  Leu  Thr  Ile  Ala  Asn  Asn  Asp  Glu  Lys  Asn  Asp  Phe  Glu  Asp  Phe
              115                      120                      125

Ile  Lys  Asn  Arg  Glu  Asn  Asp  Leu  Gln  Met  Leu  Leu  Val  Thr  Thr  His
         130                      135                      140

Glu  Lys  Ala  Met  Lys  His  Lys  His  Phe  Val  Lys  Gly  Lys  Thr  Ala  Pro
```

-continued

| | 145 | | | | 150 | | | | 155 | | | | 160 | |
|---|---|---|---|---|---|---|---|---|---|---|---|---|---|---|
| Leu | Asp | Cys | Leu | Gln<br>165 | Ser | Ala | Leu | Ile | Thr<br>170 | Pro | Arg | Glu | Thr | Glu<br>175 | Val |
| Leu | Phe | Leu | Val<br>180 | Ser | Arg | Gly | Asn | Thr<br>185 | Tyr | Lys | Glu | Val | Ser<br>190 | Arg | Thr |
| Leu | Gly | Ile<br>195 | Ser | Glu | Ala | Thr | Val<br>200 | Lys | Phe | His | Ile | Asn<br>205 | Asn | Ser | Val |
| Arg | Lys<br>210 | Leu | Asn | Val | Ile | Asn<br>215 | Ser | Arg | His | Ala | Ile<br>220 | Ser | Lys | Ala | Leu |
| Glu<br>225 | Leu | Asn | Leu | Phe | Arg<br>230 | Ala | Phe | Thr | Gly | Ser<br>235 | Leu | Met | Thr | Arg | Lys<br>240 |
| Leu | Val | Ala | Ile | | | | | | | | | | | | |

PROCESS FOR ACTIVATING GENE EXPRESSION IN BACTERIA

The present invention relates to a process for activating bacterial gene expression and in particular to a process for activating cryptic gene expression, that is, the expression of genes which are not normally expressed or silent. More particularly, the present invention relates to a process for the activation of cryptic gene expression to produce bioactive compounds including antibiotics such as carbapenems.

The carbapenem antibiotics constitute a diverse group of β-lactam antibiotics characterised by potent anti-bacterial and β-lactamase—resistent activity. More than forty different carbapenems are known, most of which are produced by the actinomycetes, particularly Streotomyces spp (Ratcliffe and Albers-Schonberg, 1982; Brown 1984; Williamson 1986; all cited in Bainton et al 1992).

Carbapenems have been isolated from the Gram-negative bacterium *Serratia marcescens* and *Erwinia carotovora* by Parker et al. (1982) and in *Azospirilium spp* UK 1521 by Kintaka et al. (1985); all cited in Bainton et al 1992.

The regulatory mechanisms involved in the control of carbapenem biosynthesis remain largely unknown. However, Bainton et al (1992) have recently shown that carbapenom biosynthesis is regulated by the regulatory factor N-(3-oxohexanoyl)-L-homoserine lactone (HSL). This compound was previously only known for its role in auto-induction of bioluminescence in the marine bacterium *Vibrio fischer*. HSL is also structurally related to the A- and I-factors which are known to regulate production of antibiotics in some Streptomyces species.

In order to examine the biosynthetic and regulatory mechanisms involved in the production of the β-lactam antibiotic 1-carbapen-2-em-3-carboxylic acid by *Erwinia carotovora*, blocked mutants were obtained with a carbapenem non-producing phenotype (Caf) as described by Bainton et al (1992). These mutants fell into two distinct groups: group 1 mutants secreted a low molecular mass diffusible factor which restored carbapenem biosynthesis in group 2 mutants, but not vice versa. This factor was shown to be HSL. Class 1 mutants produced HSL and were thus thought to be defective in carbapenenem biosynthatic genes.

In order to study class 1 mutants a chromosomal DNA cosmid library of *Erwinia carotovora* ATCC39048 was constructed in *Escherichia coli*. The cosmids produced were used in standard complementation studies to find a esquence which could restore the carbapenem antibiotic production in the class 1 mutants.

One cosmid (cWU142) was presumed to contain the carbapenem biosynthetic genes. Restriction fragments of this cosmid were sub-cloned and a 3.8 Kb EcoRI fragment was found to complement 7 out of 8 class 1 mutants. This fragment was sequenced and shown to comprise 2 Kb of cosmid DNA and 1.8 Kb of Erwinia DNA. This was extremely unexpected because known antibiotic biosynthetic gene sequences are much longer than 1.8 Kb.

The 1.8 Kb gene sequence was found to encode CarR a homologue of the LuxR regulatory protein from the Lux operon system associated with the bioluminescence phenotype of the marine bacterium *V. fischeri*.

By analogy with the *V. fischeri* Lux system, the inventors postulated that when HSL is made, it binds to CarR which can then act as a transcriptional activator of the carbapenem biosynthetic genes. Thus, the inventors reasoned that 7 out of 8 of the class 1 mutants are not, as expected, defective in genes required for synthesis of carbapenem, but in a gene encoding a regulatory protein, CarR, needed to switch on the carbapenem biosynthetic genes. Without the CarR gene product the carbapenem biosynthetic genes are not expressed, that is, they remain silent or cryptic.

By similar methods of those described for the construction of the *Erwinia carotovora* cosmid library, we have also made a pSF6 chromosomal library of a strain of *Serratia marcescens* that makes the same carbapenem (1-carbapen-2-em-3-carboxylic acid) as the Erwinia strain, but does not make HSL. We packaged this cosmid library into bacteriophage Lambda and used this lysate to transduce the class 1 car⁻ mutants of Erwinia. A cosmid (pNRT1) complemented the class 1 mutants. This cosmid was subcloned to a small BamH1 fragment of approximately 3 Kb which still complemented the class 1 mutants. Sequence analysis of the relevant complementing gene revealed that it encoded a homologue of the Erwinia CarR protein, as predicted. The Erwinia and Serratia genes hybridise to each other. The Serratia CarR protein must act in a lactone-independent way, as the cognate host does not produce HSL.

Antibiotic production by bacteria is relatively rare, for example, only two out of forty-five (4%) strains of *E.carotovora* tested produced antibiotic.

Consequently, it is generally necessary to screen vast numbers of bacterial isolates in the search for novel antibiotics for example, Sykes et al (1981) screened over one million isolates and were able to identify only seven antibiotic producers.

Clearly, any means of increasing the incidence of antibiotic production in bacteria will increase the chances of finding novel antibiotics for a given number of isolates screened.

According to the invention there is provided a DNA sequence encoding the CarR gene product or a homologue or variant thereof which, on expression in bacteria is capable of activating gene expression.

The gene will encode a polypeptide involved in synthesis of a bioactive compound and advantageously the bioactive compound comprises an antibiotic, with a carbapenem being a preferred example.

Preferably, the DNA sequence is capable of activating gene expression in a lactone-independent manner. This is desirable since it obviates the requirement for a lactone such as HSL to be present endogenously or supplied exogenously to the bacteria.

The invention also provides the DNA sequence of FIG. 1 (SEQ ID NO:1) or a sequence related thereto by virtue of the degeneracy of the genetic code, or a sequence which will hybridise to either of said sequences and which codes for a polypeptide capable of activating bacterial gene expression.

In addition, the invention also provides the DNA sequence of FIG. 2 (SEQ ID NO:3) or a sequence related thereto by virtue of the degeneracy of the genetic code, or a sequence which will hybridise to either of said sequences and which codes for a polypeptide capable of activating bacterial gene expression.

In a further aspect the invention provides a bacterial expression vector comprising a DNA sequence as described above and vector DNA.

Conveniently, the vector further comprises a sequence which on expression leads to the production of a lactone.

Advantageously, the vector further includes a sequence which codes for one or more of the carbapenem biosynthetic genes.

In another aspect, the invention provides a method of activating gene expression in bacteria comprising inserting a DNA sequence on a vector as described previously into bacteria so that it is expressed.

As will be apparent to a skilled worker, in certain bacterial hosts it may be necessary to employ regulatory sequences appropriate to those hosts to allow the sequences of the invention to be expressed.

Any vector which replicates in the bacterial cell of interest can be used in the method of the invention. However, it should not contain any penicillin-resistance where the antibiotic to be assayed is a carbapenem because this would interfere with the assay.

The vector can be inserted by any of the standard techniques such as conjugation, transformation, electroporation and transduction.

Where the DNA sequence does not activate gene expression in a lactone-independent manner, the bacteria may also be treated with a lactone and preferably HSL. Other lactones can be used such as those described by CHHABRA et al. (1993) and Zhang et al (1993).

The inventors have found that in approximately 18% of strains of *Erwinia carotovora* subspecies *carotovora* tested, transfer of the carR gene alone is sufficient to enable antibiotic production in strains which make no antibiotic naturally. These strains may have a mutant carR or they may be deleted for this gene. The antibiotic produced by carR in one such strain (SCRI193) using the above method of the invention has been shown to be identical to the carbapenem of ATCC39048. However, it is likely that structurally-modified versions of the molecule will be made in some cases or that novel antibiotics structurally unrelated to carbapenem will be made. Furthermore, if different bioassays are used it may be that totally different bioactive molecules will be discovered when the corresponding cryptic genes are activated by carR. This is a particular advantage of the present invention.

The inventors have also found that carR can switch on antibiotics in a strain of Serratia. The fact that some strains of Serratia and some streptomycetes make carbapenems strongly suggests that the carbapenem biosynthetic genes will be very widely distributed in bacteria, but will be cryptic. Given a wide distribution of genetically silent car genes in bacteria, the ability to activate them and others encoding bioactive molecules with carR, using the present invention provides a novel route for the discovery of useful molecules of interest to the pharmaceutical and agricultural industries. The "natural resources", that is, the bacterial strains which are the "reagents" for this new technique, can be isolated easily from the natural environment and so their supply is essentially unlimited. Thus, the potential for the discovery of novel modified carbapenems and other bioactive molecules is great.

The invention also provides a bioassay method for identifying bioactive compound producing bacteria comprising activating expression of genes encoding bioactive compounds by any of the above methods of the invention and screening the bacteria for the production of bioactive compounds. Preferably the bioactive compound is an antibiotic with a carbapenem being a preferred example.

In another aspect the invention provides a polypeptide encoded by any of the above DNA sequences of the invention and the use of said polypeptide to activate gene expression in bacteria.

BRIEF DESCRIPTION OF THE DRAWINGS

An embodiment of the invention will now be described, by way of example only, with reference to the accompanying drawings in which FIG. 1 (SEQ ID NOS:1 and 2) shows the DNA sequence of the carR gene of *E. carotovora* encoding the polypeptide whose amino acid sequence is also given.

FIG. 2 (SEQ ID NO:3)shows a DNA sequence comprising an SsP I restriction fragment containing the sequence of FIG. 1 (SEQ ID NO:1) and which on insertion into Erwinia strains is capable of activating antibiotic production. FIG. 3 (SEQ ID NOS:4 and 5)shows the DNA sequence of the Serratia carR gene and the HSL-independent protein product thereof.

REFERENCES

1. BAINTON et al J Biochem (1992) 288, 997–1004.
2. CHHABRA et al (1993) J. Antibiotics vol 46 No. 3, 441–454.
3. Sykes et al (1981) Nature vol. 291 489–491.
4. Zhang et al (1993) Nature vol. 362 446–448.
5. Williamson et al (1985) J. Biol Chem 4637–4647.
6. Bainton et al (1992a) Gene 116 87–91.

1. Isolation of a restrictionless mutant of the carbapenem-producing strain

A strain of *Erwinia carotovora* subspecies *carotovora* (ATCC39048) which makes the antibiotic 1-carbapen-2-em-3-carboxylic acid (carbapenem) was first made restrictionless by the following method.

The plasmid pTROY9 ($tc^R$; LamB•) was transferred to ATCC39048 by conjugal mobilisation from an *E. coli* donor strain to make strain GS100 (ATCC39048 (pTROY9)). This strain could be infected with phage λ::Tn5 and a $Kn^R$ transductant was selected. This transductant (GS101) was shown to be both restrictionless and modificationless by the efficiency of plating of 4 Erwinia bacteriophages on GS101 and GS100. Strain GS101 became sensitive to transposon mutagenesis using other λ transposon delivery systems eg. λ::TnblaM (using spectinomycin $Sp^R$ as selection).

2. Isolation of Carbapenem-Negative Mutants.

Strain GS101 was mutagenised with EMS (ethane-methane sulphonate) or NTG (N-methyl-N-nitro-N-nitrosoguanidine) and survivors were screened for antibiotic production on an *E. coli* strain supersensitive to β-lactam antibiotics (strain ESS). Carbapenem non-producers (Car-) were identified.

3. The Car- Mutants fall into 2 Distinct Groups Defined by Crossfeeding

Mutants in class 1 crossfeed class 2 mutants allowing them to make antibiotic on co-cultivation. The crossfeeding molecule is N-(3-oxohexanoyl)-L-homoserine lactone (HSL)—the "autoinducer" of the bioluminescent marine bacterium *Vibro fischeri*—and is freely diffusible. HSL is made by the wild type strain and in a growth phase dependent, cell density dependent way. HSL synthesis is enabled by a gene which encodes a protein which is a homologue of the *V. fischeri* LuxI protein. (HSL is thought to bind to the LuxR protein of *V. fischeri* thereby allowing it to act as a transcriptional activator of the lux operon). The class 2 mutants fail to make HSL and so cannot switch on the car biosynthetic genes. Exogenous supply of HSL switches on antibiotic production in class 2 mutants. Class 1 mutants were presumed to be defective in the car biosynthetic genes. HSL is made by class 1 mutants.

The methods set out in paragraphs 1 to 3 are described in Bainton et al (1992).

4. Construction of a Chromosomal Gene Library of Strain ATCC39048

The chromosomal DNA was prepared by standard methods and a cosmid library in *E. coli* was constructed in the broad host range cosmid pSF6 ($Sp^R$ selection). This was packaged in vitro into phage particles by standard methods. In principle any cosmid vector or plasmid vector would be suitable, as long as it has no penicillin-resistance genes which would interfere with the carbapenem bioassay.

5. Complementation of the Class 1 and Class 2 Mutants from the Cosmid Library: Cloning the Car Genes A class 1 mutant (mutant 14) and a class 2 mutant (mutant 23) were transduced with the cosmid library and transductants were selected on Sp-containing agar. Transductants were screened for restoration of antibiotic producing using the ESS strain assay for method (see Bainton et al (1992)). Complementing cosmid clones were isolated for each class of mutants. The class 1 cosmid (cWU142) was presumed to contain the car biosynthetic genes. Restriction fragments from this cosmid were subcloned and a 3.8 Kb EcoRI fragment complemented 7 of the 8 class 1 mutants. This fragment was sequenced. 2 Kb of this was original vector DNA and the 1.8 Kb Erwinia DNA only appeared to carry one obvious gene. This gene encoded a homologue of LuxR—named carR. The carR gene alone is capable of complementing most of the class 1 mutants which were thought to be car biosynthetic mutants. Thus most of these mutants are regulatory mutants. Presumably, by analogy with the *V. fischeri* Lux system, when HSL is made, it binds to CarR and can then act as a transcriptional activator of the car biosynthetic genes.

6. Production of HSL is Widely Distributed in Bacteria; at least 50% of *E. caratovora* make a Small Molecule which can Crossfeed Class 2 Mutants.

Using the crossfeeding of class 2 mutants for antibiotic production as a crude bioassay we showed that over 50% of *E. carotovora* strains in a culture collection could crossfeed for carbapenem production. We knew that this was a relatively crude assay and that the figure given above was a gross underestimate, because we also knew that many diverse bacterial species make HSL and related molecules (Bainton et al 1992a); Zhang et al (1993). By using the bioluminescence assay of Bainton et al (1992a) we have shown that much higher percentages (up to 100%) are detectable as HSL producers.

7. Activation of Cryptic Antibiotic Production Genes by carR

Natural antibiotic production by these Ecc strains is relatively rare (approximately 4%) but in most strains which are presumptive HSL producers the cWU142 cosmid enables antibiotic production—presumably because the endogenous HSL binds to the CarR protein and switches on the car biosynthetic genes on cWU142. However, in approximately 18% of strains which do not normally produce antibiotic, transfer of the carR gene alone is sufficient to enable antibiotic production.

Thus, carR can activate antibiotic synthesis genes which are not normally expressed in some *E. carotovora* strains. These strains may have a mutant carR or they may be deleted for this gene. The antibiotic switched on by carR in one such strain (SCRI193) has been shown to be identical to the carbapenem of ATCC39048.

We have also confirmed that SCRI 193 contains a non-functional mutant form of the CarR protein, but a functional set of carbapenem biosynthetic genes. (The mutant form of CarR in SCRI 193 has 14 amino acid alterations [in total] at different parts of the protein.)

However, it is likely that structurally-modified versions of this antibiotic will be made in some cases; or that novel antibiotics structurally unrelated to carbapenem will be made. Furthermore, if a different bioassay is used, totally different bioactive molecules may be discovered which can be synthesised when the corresponding cryptic genes are activated by the carR gene product or homologues or variations thereof.

The gene encoding the CarR protein has been shown to be capable of switching on synthesis of normally cryptic antibiotics.

The literature describes very few strains of bacteria which make carbapenem antibiotics. These include a few strains of Erwinia, Serratia and Streptomyces (Parker et al 1982, Shionogi 1985; both cited in Williamson 1985). However, the inventors have shown that by using the carR gene according to the invention, many strains of Erwinia can be activated to produce antibiotic. By analogy with the results obtained with Erwinia it is clear that a similar effect will be obtained in other bacteria taxonomically distinct from Erwinia.

It will also be possible to activate such cryptic genes using CarR alone or with exogenously added HSL or a related lactone or spent culture supernatants. Given a wide distribution of genetically silent car genes in bacteria, an ability to activate them (and others encoding bioactive molecules via carR or homologues or variants thereof) provides a novel route to discovery of useful molecules of interest to the pharmaceutical and agricultural industries. The "natural resources" ie. the bacterial strains which are the "reagents" for this new technique, are effectively unlimited because they can easily be isolated from the natural environment and so the potential for discovery of novel modified carbapenems and other bioactive molecules is great.

We claim:

1. An isolated DNA sequence encoding the CarbapenemR (CarR) gene product which, on expression in bacteria, activates carbapenem gene expression.

2. The isolated DNA sequence of FIG. 1 (SEQ ID NO:1) or a sequence related therto by virtue of the degeneracy of the genetic code, which encodes a polypeptide which activates bacterial gene expression.

3. The isolated DNA sequence of FIG. 2 (SEQ ID NO:2) or a sequence related thereto by virtue of the degeneracy of the genetic code, which encodes a polypeptide which activates bacterial gene expression.

4. A method of activating gene expression in bacteria comprising transforming said bacteria with the vector of claim 8.

5. A bioassay method for identifying bioactive compound producing bacteria comprising activating bioactive compound synthesis in bacteria using a method as claimed in claim 4, and screening the bacteria for the production of a bioactive compound.

6. A method as claimed in claim 5, wherein the bioactive compound is an antibiotic.

7. A method as claimed in claim 6 wherein the antibiotic is a carbapenem.

8. A DNA sequence as claimed in claim 1, wherein the DNA sequence activates gene expression in a lactone-independent manner.

9. A polypeptide encoded by the DNA sequence of claim 8.

10. A bacterial expression vector comprising the DNA sequence of any one of claims 1 or 2.

11. A vector as claimed in claim 10 further comprising a sequence which on expression leads to the synthesis of a lactone.

12. A vector as claimed in claim 11 which further includes a sequence comprising one or more of the carbapenem biosynthetic genes.

13. A polypeptide encoded by the DNA sequence of any one of claims 1, 2 and 3.

14. A method of activating gene expression in bacteria comprising transforming said bacteria with a bacterial expression vector comprising the DNA sequence as claimed in any one of claims 1, 2 and 3; wherein the bacteria are also treated with a lactone.

15. A method as claimed in claim 14, wherein the lactone is N-(3-oxohexanoyl)-L-homoserine lactone (HSL).

16. A bioassay method for identifying bioactive compound producing bacteria comprising activating bioactive compound synthesis in bacteria using a method as claimed in claim 15, and screening the bacteria for the production of a bioactive compound.

17. A bioassay method for identifying bioactive compound producing bacteria comprising activating bioactive compound synthesis in bacteria using a method as claimed in claim 14, and screening the bacteria for the production of a bioactive compound.

18. The DNA of claim 2 or 3, wherein said polypeptide activates carbapenem gene expression.

* * * * *